(12) United States Patent
Gu

(10) Patent No.: US 10,197,496 B2
(45) Date of Patent: Feb. 5, 2019

(54) REAL-TIME MONITORING OF MATERIAL COMPOSITION FOR QUALITY CONTROL

(71) Applicant: Empire Technology Development LLC, Wilmington, DE (US)

(72) Inventor: Yansong Gu, Bellevue, WA (US)

(73) Assignee: Empire Technology Development LLC, Wilmington, DE (US)

( * ) Notice: Subject to any disclaimer, the term of this patent is extended or adjusted under 35 U.S.C. 154(b) by 152 days.

(21) Appl. No.: 14/747,962

(22) Filed: Jun. 23, 2015

(65) Prior Publication Data

US 2016/0377535 A1 Dec. 29, 2016

(51) Int. Cl.
*G01N 21/3577* (2014.01)
*G01N 33/14* (2006.01)
*G01N 33/02* (2006.01)
*G01N 21/31* (2006.01)

(52) U.S. Cl.
CPC ....... *G01N 21/3577* (2013.01); *G01N 33/025* (2013.01); *G01N 33/14* (2013.01); *G01N 2021/3133* (2013.01); *G01N 2201/0627* (2013.01)

(58) Field of Classification Search
CPC ... G01N 2021/3133; G01N 2201/0627; G01N 21/3577
See application file for complete search history.

(56) References Cited

U.S. PATENT DOCUMENTS

| | | | | |
|---|---|---|---|---|
| 3,746,869 A | * | 7/1973 | Lindstedt | G01N 21/255 250/227.11 |
| 4,678,913 A | * | 7/1987 | Dodd, Jr. | G01N 21/3577 250/339.05 |
| 5,048,524 A | * | 9/1991 | Bailey | A61B 5/14535 600/327 |

(Continued)

OTHER PUBLICATIONS

"Brix," Wikipedia, Retrieved from URL: https://web.archive.org/web/20141218081642/http://en.wikipedia.org/wiki/Brix, , On Jan. 27, 2015, last modified on Nov. 29, 2014, pp. 1-6.

(Continued)

*Primary Examiner* — Tri Ton
*Assistant Examiner* — Rufus Phillips

(57) ABSTRACT

Technologies are generally described for determination and analysis of an optical profile of a liquid-based material to implement real-time monitoring of a composition of the liquid-based material for quality control. An imaging sub-system may include a plurality of illumination sources configured to illuminate the liquid-based material with light, and one or more detectors. The detectors may be configured to detect light reflected from a first surface of the liquid-based material, light reflected from a second surface of the liquid-based material, and/or light transmitted through the first surface and the second surface of the liquid-based material in response to the illumination. An analytics sub-system coupled to the imaging sub-system may be configured to analyze the detected light to determine an optical profile of the liquid-based material, and monitor the optical (Continued)

profile in real-time to detect changes in the optical profile indicative of corresponding changes to a composition of the liquid-based material.

14 Claims, 11 Drawing Sheets

(56) References Cited

U.S. PATENT DOCUMENTS

| | | | |
|---|---|---|---|
| 5,049,742 A * | 9/1991 | Hosonuma | F16N 29/00 250/301 |
| 6,754,600 B2 | 6/2004 | Hashimoto et al. | |
| 6,847,447 B2 | 1/2005 | Ozanich | |
| 9,322,773 B2 * | 4/2016 | Coates | G01F 23/292 |
| 2001/0055116 A1 | 12/2001 | Maczura et al. | |
| 2002/0084416 A1 * | 7/2002 | Kiuchi | G01N 21/3577 250/339.12 |
| 2005/0072217 A1 * | 4/2005 | Discenzo | G01N 11/00 73/53.05 |
| 2008/0093541 A1 * | 4/2008 | Ando | G01N 21/474 250/227.11 |
| 2009/0146061 A1 * | 6/2009 | Manneschi | G01N 21/9027 250/339.12 |
| 2011/0261355 A1 * | 10/2011 | Hannel | G01J 3/0291 356/303 |
| 2013/0256534 A1 * | 10/2013 | Micheels | G01N 21/255 250/339.07 |

OTHER PUBLICATIONS

"Gladstone—Dale relation," Wikipedia, Retrieved from URL: http://en.wikipedia.org/wiki/Gladstone%E2%80%93Dale_relation, On Jan. 27, 2015, last modified on Apr. 24, 2014, pp. 1-3.

"Image sensor," Wikipedia, Retrieved from URL: https://web.archive.org/web/20150125093432/https://en.wikipedia.org/wiki/Image_sensor, On Jan. 27, 2015, last modified on Jan. 9, 2015, pp. 1-9.

"Refractometer," Wikipedia, Retrieved from URL: https://web.archive.org/web/20150109235309/http://en.wikipedia.org/wiki/Refractometer, on Jan. 27, 2015, last modified on Jan. 2, 2015, pp. 1-8.

"Snell's law," Wikipedia, Retrieved from URL: https://web.archive.org/web/20141211191251/http://en.wikipedia.org/wiki/Snell%27s_law, on Jan. 27, 2015, last modified on Dec. 6, 2014, pp. 1-9.

"Spectrophotometry," Wikipedia, Retrieved from URL: https://web.archive.org/web/20140604003759/http://en.wikipedia.org/wiki/Spectrophotometry, On Jan. 27, 2015, last modified on May 9, 2014, pp. 1-6.

* cited by examiner

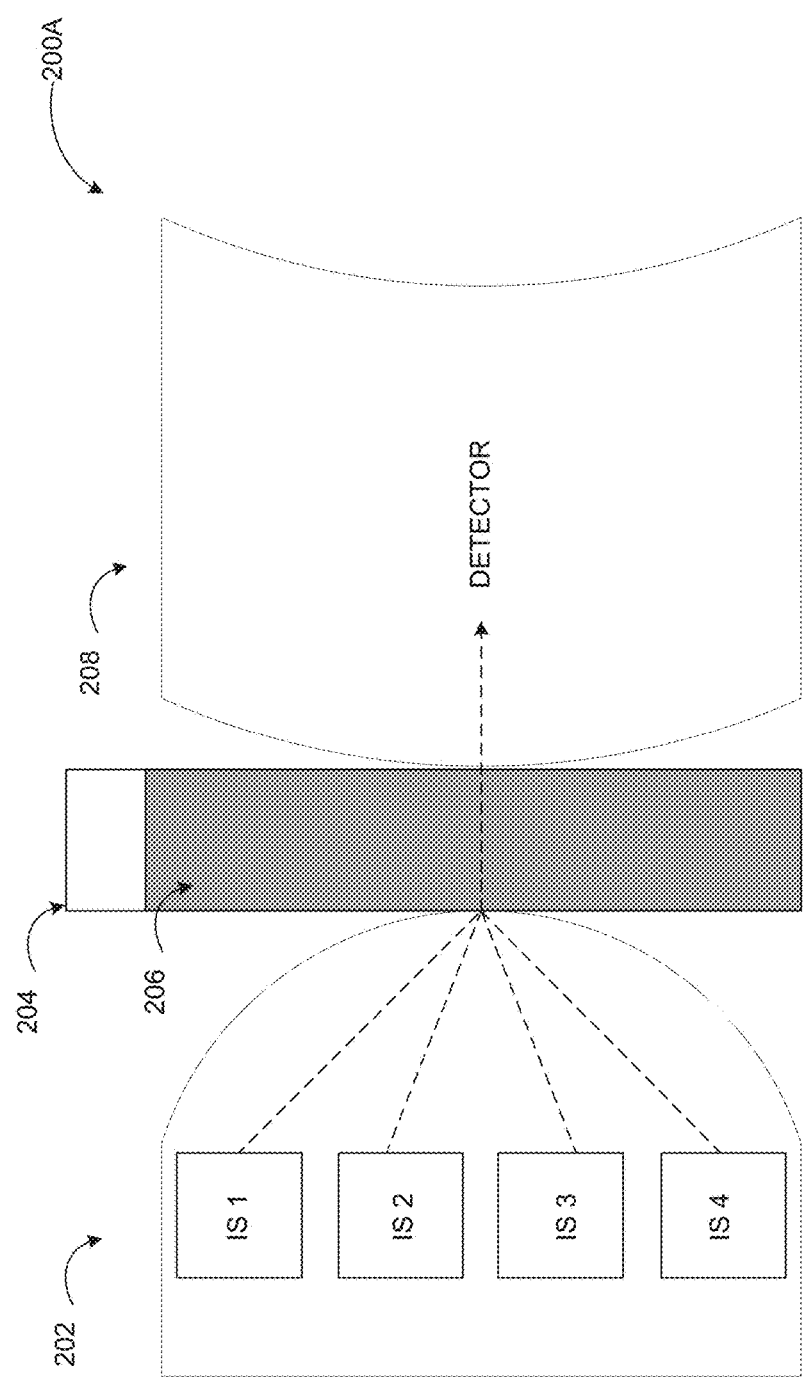

COMPUTER PROGRAM PRODUCT 900

SIGNAL-BEARING MEDIUM 902

904 ONE OR MORE INSTRUCTIONS TO

ILLUMINATE A LIQUID-BASED MATERIAL WITH LIGHT FROM A PLURALITY OF ILLUMINATION SOURCES;
DETECT LIGHT REFLECTED FROM A FIRST SURFACE OF A LIQUID-BASED MATERIAL, LIGHT REFLECTED FROM A SECOND SURFACE OF THE LIQUID-BASED MATERIAL, AND LIGHT TRANSMITTED THROUGH THE FIRST SURFACE AND THE SECOND SURFACE OF THE LIQUID-BASED MATERIAL IN RESPONSE TO THE ILLUMINATION AT ONE OR MORE DETECTORS;
ANALYZE DETECTED LIGHT TO DETERMINE AN OPTICAL PROFILE OF THE LIQUID-BASED MATERIAL; AND
MONITOR THE OPTICAL PROFILE IN REAL-TIME TO DETECT ONE OR MORE CHANGES IN THE OPTICAL PROFILE INDICATIVE OF ONE OR MORE CORESPONDING CHANGES TO A COMPOSITION OF THE LIQUID-BASED MATERIAL.

| COMPUTER-READABLE MEDIUM 906 | RECORDABLE MEDIUM 908 | COMMUNICATIONS MEDIUM 910 |

FIG. 9

REAL-TIME MONITORING OF MATERIAL COMPOSITION FOR QUALITY CONTROL

BACKGROUND

Unless otherwise indicated herein, the materials described in this section are not prior art to the claims in this application and are not admitted to be prior art by inclusion in this section.

In a variety of quality control scenarios, spectroscopic information may be acquired from a sample to analyze and/or evaluate the sample. Accordingly, current systems could benefit from e.g. improvements and/or alternative or additional solutions to enhance quality control.

SUMMARY

The present disclosure generally describes techniques for optical profile determination and analysis of a liquid-based material to implement real-time monitoring of a composition of the material for quality control.

According to some examples, an apparatus may be described. An example apparatus may include a plurality of illumination sources configured to illuminate a container with light, the container configured to contain a liquid-based material, and a controller configured to activate one or more of the illumination sources according to a predefined sequence, where each activated illumination source has a different emission wavelength. The example apparatus may also include one or more detectors configured to detect light transmitted through the liquid-based material in response to the illumination when the liquid-based material is contained in the container.

According to other examples, systems configured to monitor composition of a liquid-based material may be described. An example system may include an imaging sub-system and an analytics sub-system coupled to the imaging sub-system. The imaging sub-system may include a plurality of illumination sources configured to illuminate the liquid-based material with light, a controller configured to activate one or more of the illumination sources according to a predefined sequence, where each activated illumination source has a different emission wavelength, and one or more detectors configured to detect one or more of light reflected from a first surface of the liquid-based material, light reflected from a second surface of the liquid-based material, and light transmitted through the first surface and the second surface of the liquid-based material in response to the illumination. The analytics sub-system may include one or more processors configured to analyze detected light to determine an optical profile of the liquid-based material, and monitor the optical profile of the liquid-based material in real-time to detect one or more changes in the optical profile indicative of one or more corresponding changes to a composition of the liquid-based material.

According to further examples, methods to monitor composition of a liquid-based material are provided. An example method may include illuminating the liquid-based material with light from a plurality of illumination sources, detecting one or more of light reflected from a first surface of the liquid-based material, light reflected from a second surface of the liquid-based material, and light transmitted through the first surface and the second surface of the liquid-based material in response to the illumination at one or more detectors, analyzing detected light to determine an optical profile of the liquid-based material, and monitoring the optical profile of the liquid-based material in real-time to detect one or more changes in the optical profile indicative of one or more corresponding changes to a composition of the liquid-based material.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 2A-2C illustrate example configurations of an imaging sub-system;

FIG. 9 illustrates a block diagram of an example computer program product, all arranged in accordance with at least some embodiments described herein.

DETAILED DESCRIPTION

Figure 1:
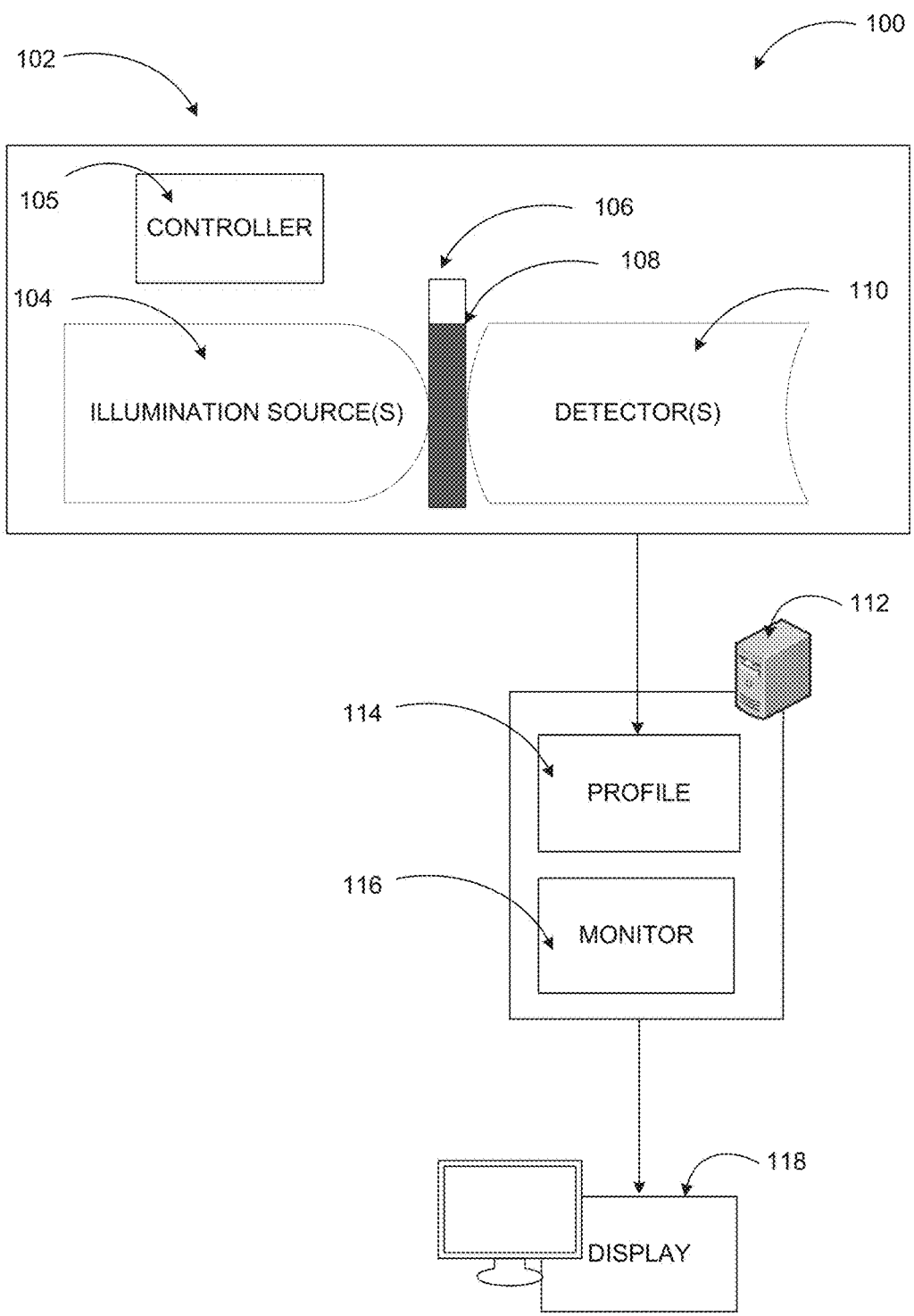
FIG. 1 illustrates an example system implemented for real-time monitoring of material composition for quality control.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to methods, apparatus, systems, devices, and/or computer program products related to determination and analysis of an optical profile of a liquid-based material to implement real-time monitoring of a composition of the material for quality control.

Briefly stated, technologies are generally described for determination and analysis of an optical profile of a liquid-based material to implement real-time monitoring of a composition of the material for quality control. An imaging sub-system may include a plurality of illumination sources configured to illuminate the liquid-based material with light, and one or more detectors. The detectors may be configured to detect light reflected from a first surface of the liquid-based material, light reflected from a second surface of the liquid-based material, and/or light transmitted through the first surface and the second surface of the liquid-based material in response to the illumination. An analytics sub-system coupled to the imaging sub-system may be configured to analyze the detected light to determine an optical profile of the liquid-based material, and monitor the optical profile in real-time to detect changes in the optical profile indicative of corresponding changes to a composition of the liquid-based material.

FIG. 1 illustrates an example system implemented for real-time monitoring of material composition for quality control, arranged in accordance with at least some embodiments described herein.

As shown in a diagram 100, an example system for real-time monitoring of material composition may include an imaging sub-system 102 and an analytics sub-system 112. In some embodiments, a liquid-based material 108 to be monitored in real-time for quality control purposes may be confined within a container 106, such as cuvettes made of plastic, glass, or fused quartz, as illustrated. The liquid-based material 108 may be a liquid, a fruit, or a vegetable, among other examples. The imaging sub-system 102 may include a plurality of illumination sources 104 and one or more detectors 110 positioned such that the illumination sources 104 may be proximal to a first portion of the container 106, and the detectors 110 may be proximal to a second portion of the container 106. In other examples, the container 106 may be a conduit, such as a tube or pipe, through which the liquid-based material may pass through, where the conduit may have a first and/or second window, which may correspond to the first and second portions of the container 106. The conduit may enable dynamic monitoring of the liquid-based material 108 dynamically as the liquid-based material 108 passes through the conduit. In further embodiments, the liquid-based material 108 may not be contained. In such embodiments, the illumination sources 104 may be proximal to a first surface of the liquid-based material 108 (or first interface of the liquid-based material 108 with the container 106) and the detectors 110 may be proximal to a second surface of the liquid-based material 108 (or second interface of the liquid-based material 108 with the container 106). The analytics sub-system 112 may be coupled via wired or wireless means to the imaging sub-system 102, and may include one or more processors configured to execute a profiling module 114 and a monitoring module 116. In some embodiments, the analytics sub-system 112 may be coupled to a display 118.

In some example embodiments, one or more of the illumination sources 104 may be configured to illuminate the container 106 containing the liquid-based material 108 with light. The light may be incident on the liquid-based material 108 through the first portion of the container 106, and light transmitted through the liquid based material 108 may leave the liquid based material 108 through the second portion of the container 106. The illumination sources 104 may be activated by a controller 105, where each activated illumination source may have a different emission wavelength. The illumination sources 104 may include light emitting diodes (LEDs), and one or more of white light sources, ultraviolet (UV) light sources, infrared light sources, red light sources, orange light sources, yellow light sources, green light sources, blue light sources, and violet light sources, for example. The controller 105 may be configured to select the illumination sources for activation based on a range of wavelengths transmitted by the liquid-based material 108. Furthermore, the controller may be configured to activate the one or more selected illumination sources according to a predefined sequence, where the sequence may be selected based on the range of wavelengths transmitted by the liquid-based material 108.

The detectors 110 may be configured to detect the light transmitted through the liquid-based material 108 in response to the illumination. For example, the position of the detectors 110 proximal to the second portion of the container 106 may enable the detectors 110 to detect light that has left the second portion of the container 106, after passing through the liquid-based material 108. The detectors 110 may include photodiodes, photomultiplier tubes, complementary metal oxide semiconductor (CMOS) image sensors, charged coupled devices (CCDs), and/or micro-channel plates. In some embodiments, at least one of the detectors 110 may be an image sensor configured to capture an image of the light transmitted through the liquid-based material 108 in response to the illumination. In other embodiments, one or more other detectors may be adjacent to or integrated with the illumination sources 104 in an imaging device proximal to the first portion of the container 106. The position of the other detectors may enable the other detectors to detect light reflected by a first surface of the liquid-based material proximal to the first portion of the container 106 (or first interface of the liquid-based material 108 with the first portion of the container 106) and light reflected by a second surface of the liquid-based material proximal to the second portion of the container 106 (or second interface of the liquid-based material 108 with the second portion of the container 106).

The processors of the analytics sub-system 112 may be configured to receive detected light from the imaging sub-system 102. The profiling module 114 may be configured to analyze the detected light to determine an optical profile of the liquid-based material 108 based on one or more of an intensity of reflection, transmission, and absorbance of the light at a respective wavelength at which the light was emitted from the illumination sources. For example, the light transmitted through the liquid-based material 108 may be analyzed to determine a transmittance and an absorbance. An intensity of the light transmitted through the liquid-based material 108 may be determined. The transmittance may be determined based on a ratio of the intensity of the light transmitted through the liquid-based material 108, and an intensity of the light emitted from the illumination sources 104. The absorbance may be determined based on the transmittance, where absorbance is equal to the inverse logarithm of transmittance. In further embodiments, where reflected light may be able to be detected from the first and/or second portions of the container 106 due to positioning of the other detectors proximal to the first portion of the container 106, an intensity of the light reflected from the first portion and the second portion of the container 106 may be determined. The intensity of the light reflected by a first surface of the liquid-based material proximal to the first portion of the container 106 and light reflected by a second surface of the liquid-based material proximal to the second portion of the container 106 in response to the illumination may then be compared to an intensity of light transmitted from the illumination sources 104.

The monitoring module 116 may be configured to monitor the optical profile in real-time to detect changes in the optical profile indicative of corresponding changes to a composition of the liquid-based material. In some embodiments, one or more characteristics including the composition of the liquid-based material 108 may be evaluated based on a comparison of the optical profile of the liquid-based material 108 to an optical profile of a reference liquid-based material.

As previously discussed, spectroscopic information may be acquired from a sample to analyze and/or evaluate the sample in a variety of quality control scenarios. According to embodiments described herein, transmitted light from the sample may be detected (and absorbed light determined from the transmitted light) in addition to reflected light, in order to determine and monitor a more complete optical profile of the sample based on the reflected light, the transmitted light, and absorbed light in real-time to enhance quality control.

Figure 2B:
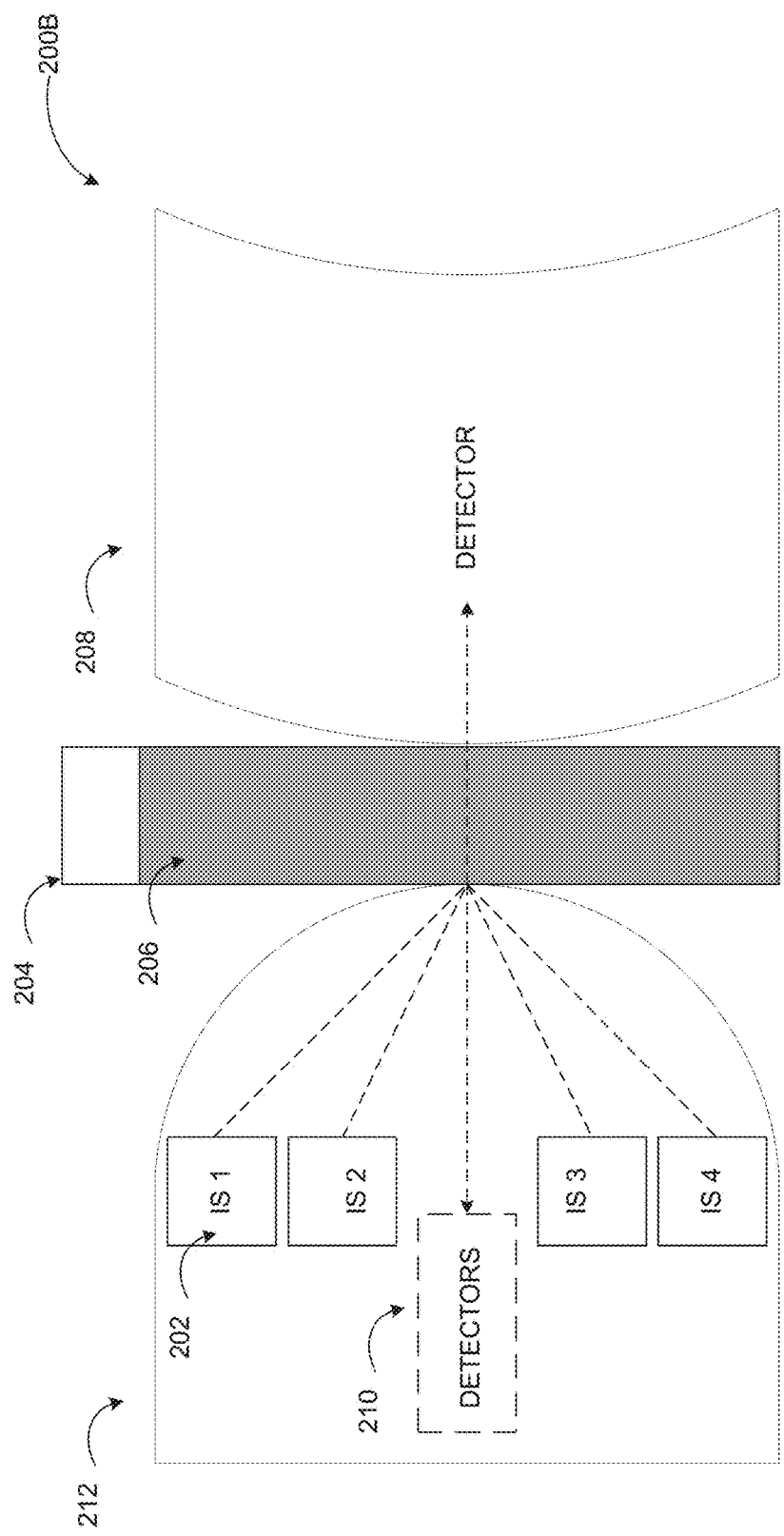
Figure 2C:
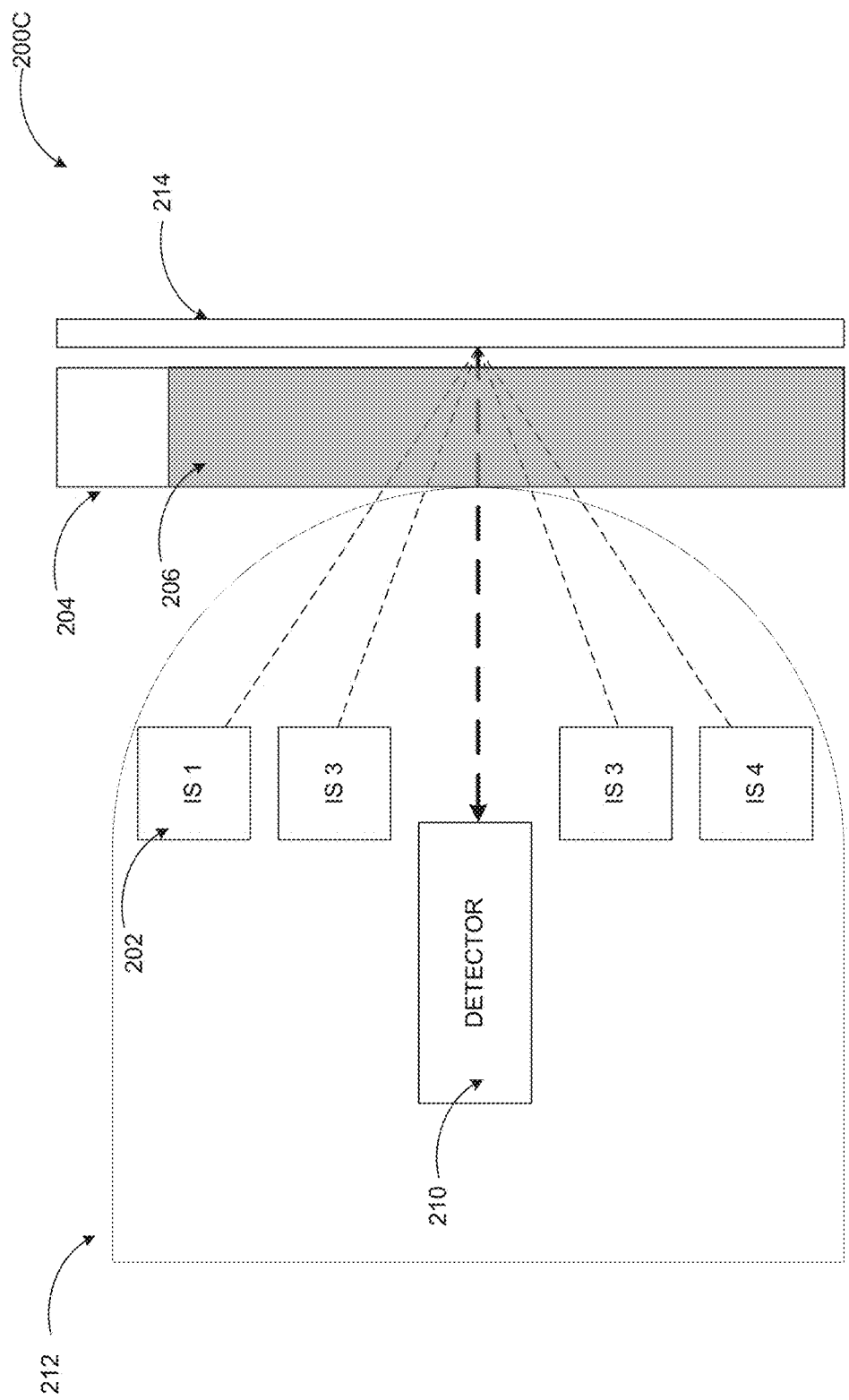

FIGS. 2A-2C illustrate example configurations of an imaging sub-system, arranged in accordance with at least some embodiments described herein.

As shown in a diagram 200A, an example imaging sub-system may include a plurality of illumination sources 202 and one or more detectors 208. The illumination sources 202 may include LEDs, and one or more of white light sources, UV light sources, infrared light sources, red light sources, orange light sources, yellow light sources, green light sources, blue light sources, and violet light sources, for example. The detectors 208 may include photodiodes, photomultiplier tubes, CMOS image sensors, CCDs, and/or micro-channel plates, for example. The illumination sources 202 and the detectors 208 may be aligned in a same horizontal plane and a same vertical plane, and a distance between the illumination sources and the one or more detectors 208 may be less than or equal to 1 centimeter apart. In some examples, the liquid-based material 206 may be confined within a container 204 that comprises at least one wall substantially transparent to the light, such as cuvette, positioned between the illumination sources 202 and the detectors 208. A depth of the liquid based-material 206, equal to the width of the cuvette, may need to be fixed and less than 5 millimeters (mm) considering a thickness of the cuvette. The container 204 may comprise crystal, glass, silicon-based material, and/or plastic for example, where the container may be reusable or disposable. The illumination sources 202 and detectors 208 may be positioned such that the illumination sources 202 may be proximal to a first portion of the container 204, and the detectors 208 may be proximal to a second portion of the container 204. In examples, where the liquid-based material is not contained, the illumination sources 202 may be proximal to a first surface of the liquid-based material 206 and the detectors 208 may be proximal to a second surface of the liquid-based material 206.

Upon sequential activation by a controller, one or more of the illumination sources 202 may be configured to illuminate the liquid-based material 206 with light, each at a different emission wavelength, where the light may be incident on the first surface of the liquid-based material 206 through the first portion of the container 204. The detectors 208 may be configured to detect light transmitted through the liquid-based material 206 as it leaves the second portion of the container 204 after passing through the liquid-based material 206 in response to the illumination. In some embodiments, at least one of the detectors 208 may be image sensor configured to capture an image of the light transmitted through the liquid-based material 206 in response to the illumination.

As shown in a diagram 200B, an example imaging sub-system may also include one or more other detectors 210 adjacent to the illumination sources 202. The illumination sources 202 and the detectors 210 may be integrated within a single imaging device 212, such as a scanner, where the imaging device 212 is proximal to the first portion of the container 204.

Upon sequential activation by a controller, one or more of the illumination sources 202 may be configured to illuminate the liquid-based material 206 with light, each at a different emission wavelength, where the light may be incident on the liquid-based material 206 through the first portion of the container 204. The detectors 210 may be configured to detect light reflected by a first surface of the liquid-based material proximal to the first portion of the container 204 and light reflected by a second surface of the liquid-based material proximal to the second portion of the container 204. As previously discussed, the detectors 208 may be configured to detect the light transmitted through the liquid-based material 206 in response to the illumination. Detection of the light reflected from and light transmitted through the liquid-based material 206 in response to the illumination may enable a more complete optical profile to be determined. For example, the optical profile may be determined based on an intensity of reflection, transmittance, and absorbance of the light at a respective wavelength, or at a plurality of respective wavelengths, at which the light was emitted from the illumination sources.

As shown in a diagram 200C, another example imaging sub-system may include the imaging device 212 comprising the illumination sources 202 and the detectors 210 adjacent to the illumination sources 202, and a reflective material 214. The imaging device 212 may be proximal to the first portion of the container 204, and the reflective material 214 may be proximal to the second portion of the container 204. In some embodiments, a second portion of the container 204 itself may be the reflective material 214.

Upon sequential activation by a controller, one or more of the illumination sources 202 may be configured to illuminate the liquid-based material 206 with light, each at a different emission wavelength, where the light may be incident on the liquid-based material 206 through the first portion of the container 204. The detectors 210 may be configured to detect light reflected by a first surface of the liquid-based material proximal to the first portion of the container 204 and light reflected by a second surface of the liquid-based material proximal to the second portion of the container 204. Due to the reflective material 214, the detectors 210 may also be configured to detect the light transmitted through the liquid-based material 206 in response to the illumination. As previously discussed, detection of the light reflected from and the light transmitted through the liquid-based material 206 in response to the illumination may enable a more complete optical profile to be determined based on an intensity of reflection, transmittance, and absorbance of the light at a respective wavelength at which the light was emitted from the illumination sources.

Figure 3:
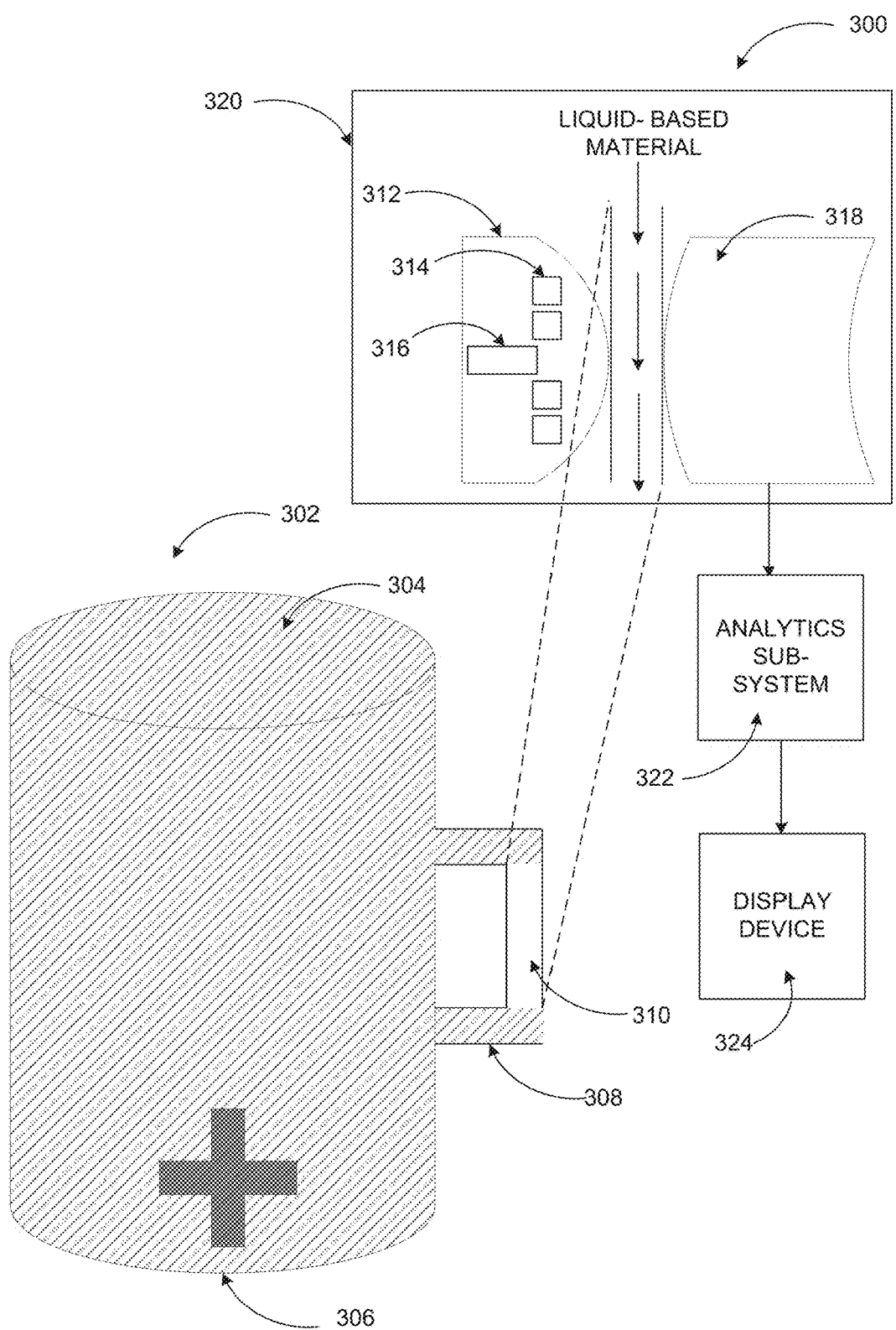
FIG. 3 illustrates an example scenario in which real-time monitoring of material composition for quality control may be implemented.

FIG. 3 illustrates an example scenario in which real-time monitoring of material composition for quality control may be implemented, arranged in accordance with at least some embodiments described herein.

As shown in a diagram 300, a vessel 302 may include a liquid-based material 304, such as wine. For quality control, a vintner may monitor various processes throughout wine production, such as a secondary fermentation and/or an aging process in real time, for example. During this period of three to six months, the wine may be stored in the vessel 302, which may comprised of stainless steel or oak, for example, and air locked to protect the wine from oxidation. Using current systems, tests are run periodically in a laboratory to analyze a composition, and various chemical and/or physical properties of the wine, where the vessel 302 may need to be opened via exit 306 to obtain a sample of the wine, breaking the airlock, and potentially degrading the quality of the wine. The tests may include, but are not limited to, Brix, pH, titratable acidity, residual sugar, free or available sulfur, total sulfur, volatile acidity and percent alcohol, for example.

According to some embodiments, an extension 308 of the vessel 302 in which the liquid-based material 304 is circulating, may include a conduit 310, such as a tube or pipe, through which the liquid-based material may pass through. The conduit 310 may have a first window and a second window comprised of crystal, silicon-based material, or plastic, for example. An imaging sub-system 320 may include a plurality of illumination sources 314, and a first set of one or more detectors 316 adjacent to the illumination sources 314 integrated within an imaging device 312, such as a scanner. The imaging device 312 may be proximal to the first window of the conduit 310. The imaging sub-system 320 may also include a second set of one or more detectors 318 that may be joined with the imaging device 312 through a connector, where the second set of detectors 318 may be proximal to the second window of the conduit 310. The connector may enable the imaging sub-system 320 to attach onto the conduit 310 such that the liquid-based material 304 may be sampled and analyzed without opening the airlock vessel 302, and enabling the liquid-based material 304 to be monitored dynamically as the liquid-based material 304 passes through the conduit 310.

For example, upon sequential activation by a controller, the illumination sources 314 may be configured to illuminate the conduit 310 with light, each at a different emission wavelength, such that the light is incident on the liquid-based material 304 through the first window of the conduit 310. The first set of detectors 316 adjacent to the illumination sources 314 may be configured to detect light reflected from the first window and the second window of the conduit 310 in response to the illumination. The second set of detectors 318 may be configured to detect light transmitted through the liquid-based material 304 as it leaves the second window of the conduit 310 after passing through the liquid-based material 304 in response to the illumination. In some embodiments, at least one of detectors from the first set of detectors 316 or second set of detectors 318 may be an image sensor configured to capture an image of the light reflected from the first and second windows of the conduit 310, or an image of the light transmitted through the first the liquid-based material 304 in response to the illumination, respectively.

The detected light may be transmitted to an analytics sub-system 322 wirelessly coupled to the imaging sub-system 320. One or more processors of the analytics sub-system 322 may be configured to analyze the detected light to determine an optical profile of the liquid-based material 304 based on an intensity of reflection, transmittance, and absorbance of the light at a respective wavelength at which the light was emitted from the illumination sources 314. For example, the processors may be configured to determine an intensity of the light reflected by a first surface of the liquid-based material proximal to the first window of the conduit 310 and light reflected by a second surface of the liquid-based material proximal to the second window of the conduit 310. The processors may then be configured to compare the intensity of the light reflected by a first surface of the liquid-based material proximal to the first window of the conduit 310 and light reflected by a second surface of the liquid-based material proximal to the second window of the conduit 310 to an intensity of light transmitted from the illumination sources 314. Additionally, the processors may be configured to determine an intensity of the light transmitted through the liquid-based material 304 in response to the illumination in order to determine a transmittance based on a ratio of the intensity of the light transmitted through the liquid-based material 304, and an intensity of the light emitted from the illumination sources 314. Furthermore, the processors may be configured to determine an absorbance based on the transmittance, where the absorbance is an inverse logarithm of the transmittance.

The processors of the analytics sub-system 322 may further be configured to monitor the optical profile of the liquid-based material 304 in real-time to detect a change in the optical profile, where a change in the optical profile may indicate a change in a composition of the liquid-based material 304. In some embodiments, the monitored optical profile may be displayed through a display device 324. The display device 324 may be integrated with an external surface of the vessel 302 or may be a separate component.

Figure 4:
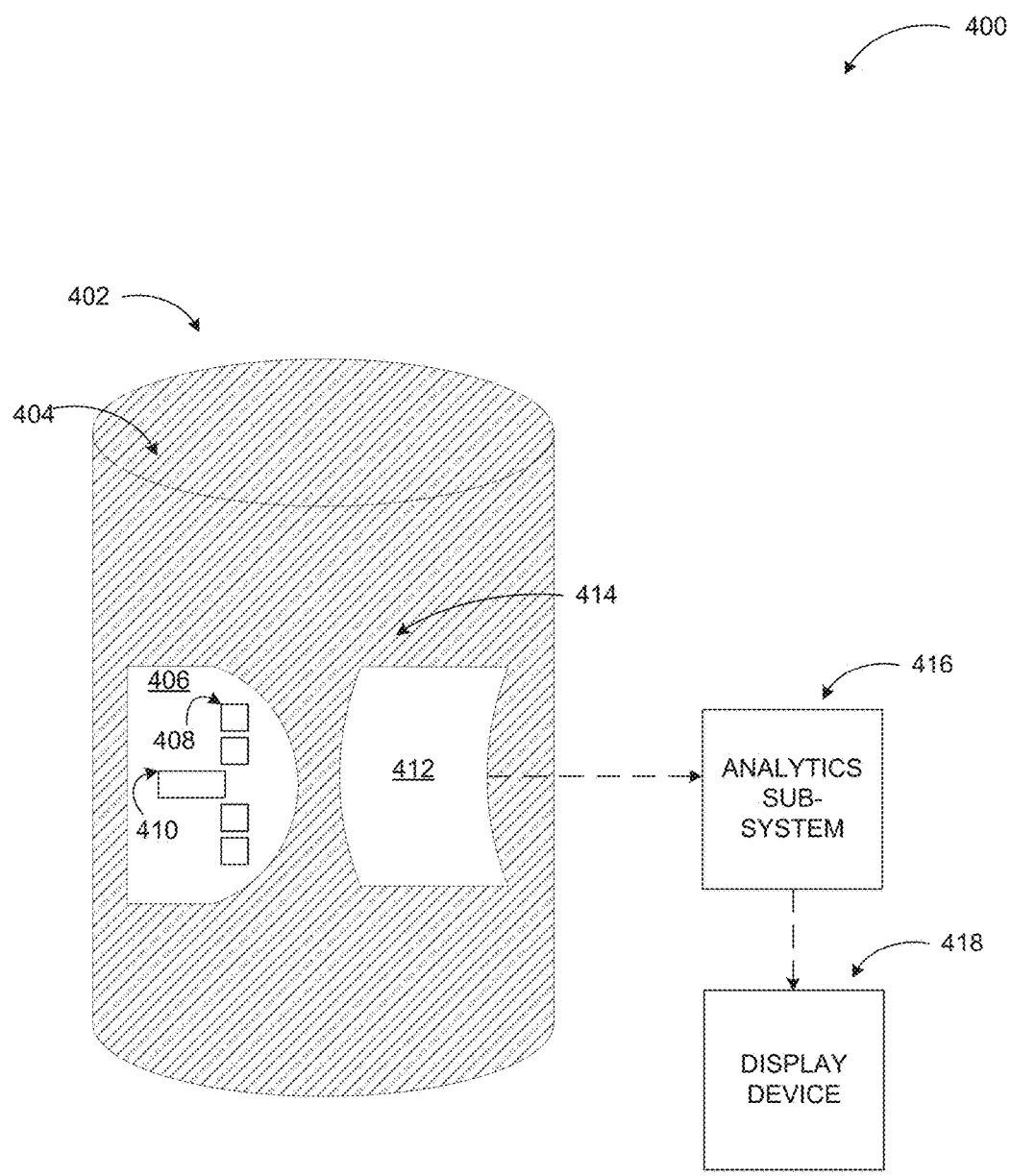
FIG. 4 illustrates another example scenario in which real-time monitoring of material composition for quality control may be implemented.

FIG. 4 illustrates another example scenario in which real-time monitoring of material composition for quality control may be implemented, arranged in accordance with at least some embodiments described herein.

As shown in a diagram 400, a vessel 402 may include a liquid-based material 404, such as wine. An imaging sub-system 414 may include a plurality of illumination sources 408 and a first set of one or more detectors 410 integrated within an imaging device 406. The imaging sub-system 414 may also include a second set of one or more detectors 412 that may be joined to the imaging device 406 through a connector. The imaging sub-system 414 may be immersed in the liquid-based material 404 within the vessel 402, such that the liquid-based material 404 may circulate between the imaging device 406 and the second set of detectors 412 for continuous sampling. The imaging device 406 may be proximal to a first surface of the liquid-based material 404, and the second set of detectors 412 may be proximal to a second surface of the liquid-based material 404.

For example, upon activation by a controller, the illumination sources 408 may be configured to illuminate the portion of the liquid-based material 404 circulating between the imaging device 406 and the second set of detectors 412 with light, each at a different emission wavelength. The first set of detectors 410 may be configured to detect light reflected from the first surface of the liquid-based material 404, and light reflected from the second surface of the liquid-based material 404 in response to the illumination. The second set of detectors 412 may be configured to detect light transmitted through the first surface and the second surface of the liquid-based material 404 in response to the illumination.

The light detected by the first set of detectors 410 and the second set of detectors 412 may be transmitted to an analytics sub-system 416 wirelessly coupled to the imaging sub-system 414. One or more processors of the analytics sub-system 416 may be configured to analyze the detected light to determine an optical profile of the liquid-based material 404, as previously discussed above in conjunction with FIG. 4A. The processors of the analytics sub-system 322 may further be configured to monitor the optical profile of the liquid-based material 404 in real-time to detect a change in the optical profile, where a change in the optical profile may indicate a change in a composition of the liquid-based material 404. In some embodiments, the monitored optical profile may be displayed through a display device 418. The display device 418 may be integrated with an external surface of the vessel 402 or may be a separate component.

Figure 5:
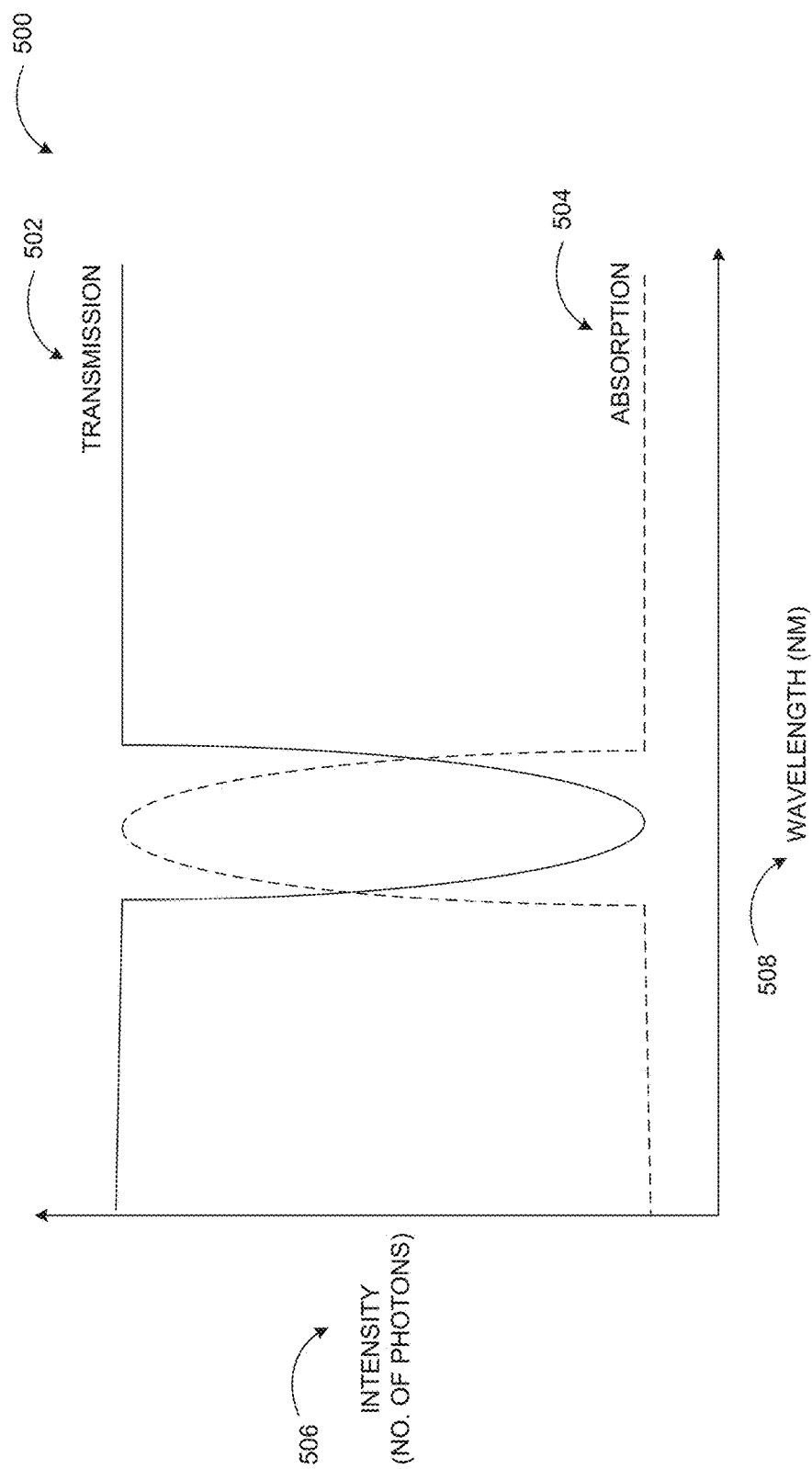
FIG. 5 illustrates an example optical profile of a liquid-based material.

FIG. 5 illustrates an example optical profile of a liquid-based material, arranged in accordance with at least some embodiments described herein.

As shown in a diagram 500, an optical profile determined for a liquid-based material according to the above described embodiments, may include a transmission spectrum 502 and an absorption spectrum 504. As previously discussed one or more illumination sources may be configured to illuminate a liquid-based material with light, where the illumination sources are activated sequentially and each at a different emission wavelength. Among other things, the detectors may be configured detect light transmitted through a first and second surface of the liquid-based material in response to the illumination, and an intensity of the light transmitted through the first and second surface of the liquid-based material may be determined. Transmittance may then be determined based on a ratio of the intensity of light transmitted through the first and second surface of the liquid-based material, and an intensity of the light emitted from the illumination sources. The transmission spectrum 502 may depict the transmittance (intensity 506) of the light at a respective wavelength at which the light was emitted from the illumination sources (wavelength 508). Absorbance may be determined based on the transmittance, where the absorbance is an inverse logarithm of the transmittance. As such the absorption spectrum 504 and the transmission spectrum 502 have an inverse relationship as clearly illustrated by the shape of the spectra in the diagram 500. The optical profile determined for the liquid-based material may also include a profile of the reflected light from the first and second surfaces of the liquid-based material. The reflected light profile may be determined based on an intensity of the reflected light from the first and second surfaces of the liquid-based material at the respective wavelength at which the light was emitted from the illumination sources (wavelength 508).

Figure 6:
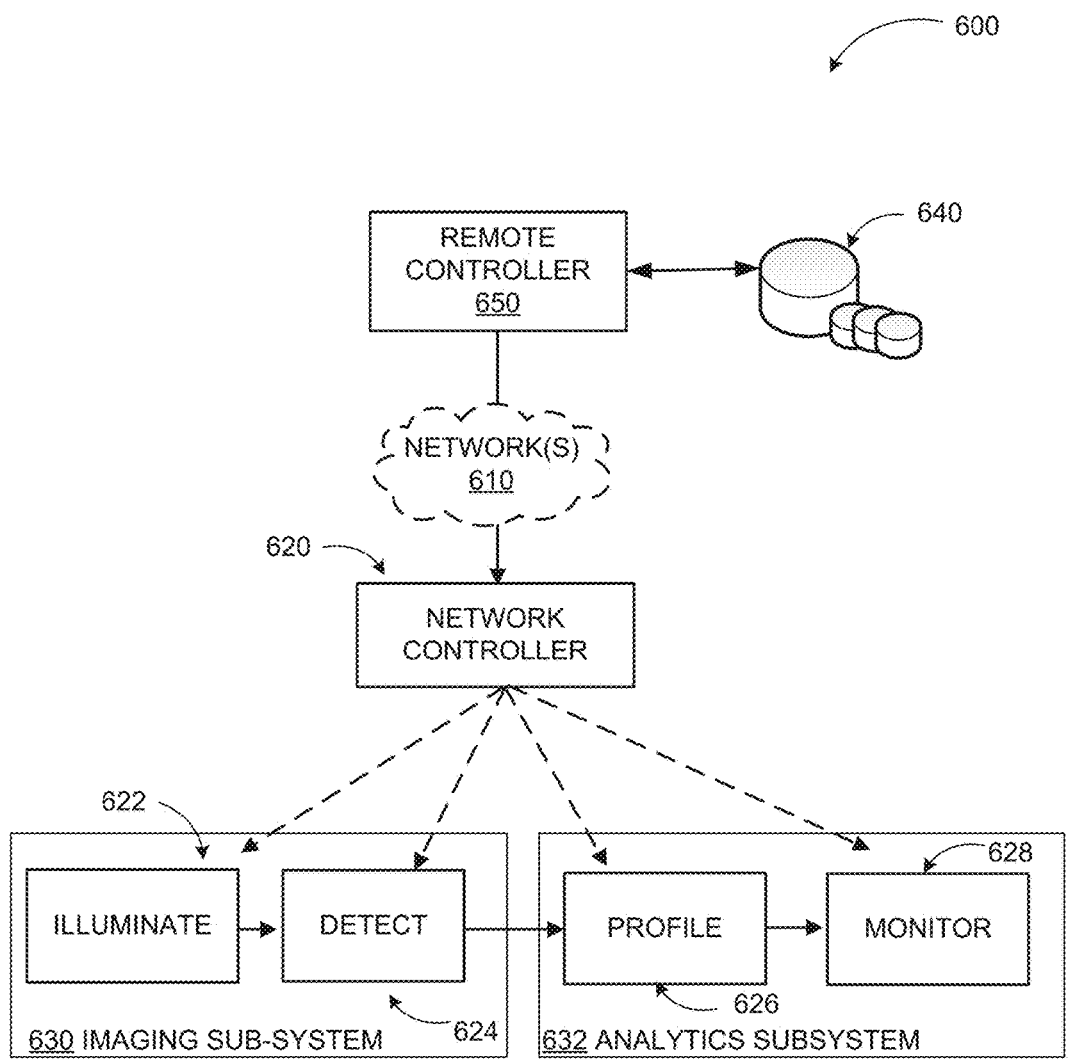
FIG. 6 illustrates an example system configured to implement real-time monitoring of material composition for quality control.

FIG. 6 illustrates an example system configured to implement real-time monitoring of material composition for quality control, arranged in accordance with at least some embodiments described herein.

System 600 may include at least one controller 620, at least one illumination module 622 and at least one detection module 624 of an imaging sub-system 630, at least one profiling module 626 and at least one monitoring module 628 of an analytics sub-system 632. The controller 620 may be operated by human control or may be configured for automatic operation, or may be directed by a remote controller 650 through at least one network (for example, via network 610). Data associated with controlling the different processes of production may be stored at or received from data stores 640.

The illumination module 622 of the imaging sub-system 630 may be configured to illuminate a liquid-based material with light from a plurality of illumination sources. The illumination sources may include LEDs, and one or more of white light sources, UV light sources, infrared light sources, red light sources, orange light sources, yellow light sources, green light sources, blue light sources, and violet light sources, for example. A controller of the imaging sub-system 630 may be configured to active the illumination sources, where each activated illumination source may have a different emission wavelength. In some embodiments, the controller may be configured to select one or more of the illumination sources for activation based on a range of wavelengths reflected by the liquid-based material such that an emission wavelength of each activated illumination source corresponds to the range of wavelengths reflected by the liquid-based material. In other embodiments, the controller may be configured to select one or more of the illumination sources for activation based on a range of wavelengths transmitted by the liquid-based material. Furthermore, the controller may be configured to activate the one or more selected illumination sources according to a predefined sequence, where the sequence may be selected based on the range of wavelengths reflected and/or transmitted by the liquid-based material.

The detection module 624 of the imaging sub-system 630 may be configured to detect light reflected from and light transmitted through the liquid-based material in response to an illumination at one or more detectors. The detectors may include photodiodes, photomultiplier tubes, CMOS image sensors, CCDs, and/or micro-channel plates, for example. A first set of the detectors may be integrated with the illumination sources in a single imaging device that is positioned proximal to a first surface of the liquid-based material (or if the liquid-based material is contained within a container, a first portion of the container). The first set of the detectors may be configured to determine the light reflected from the first and second surface of the liquid-based material. A second set of the detectors may be positioned proximal to a second surface of the liquid-based material (or if the liquid-based material is contained within a container, a second portion of the container) in order to detect the light transmitted through the first surface and the second surface of the liquid-based material. The detected light may then be transmitted, through wired or wireless means, to the analytics sub-system 632 coupled to the imaging sub-system 630.

The profiling module 626 of the analytics sub-system 632 may be configured to analyze the detected light to determine an optical profile of the liquid-based material based on one or more of an intensity of reflection, transmittance, and absorbance of the light at a respective wavelength at which the light was emitted from the illumination sources. The monitoring module 628 of the analytics sub-system 632 may then be configured to monitor the optical profile of the liquid-based material in real-time to detect changes in the optical profile indicative of corresponding changes to a composition of the liquid-based material. In some embodiments, the monitored optical profile may be displayed through a display device.

The examples in FIGS. 1 through 6 have been described using specific apparatuses, configurations, and systems for real-time monitoring of material composition for quality control. Embodiments for implementing real-time monitoring of material composition are not limited to the specific apparatuses, configurations, and systems according to these examples.

Figure 7:
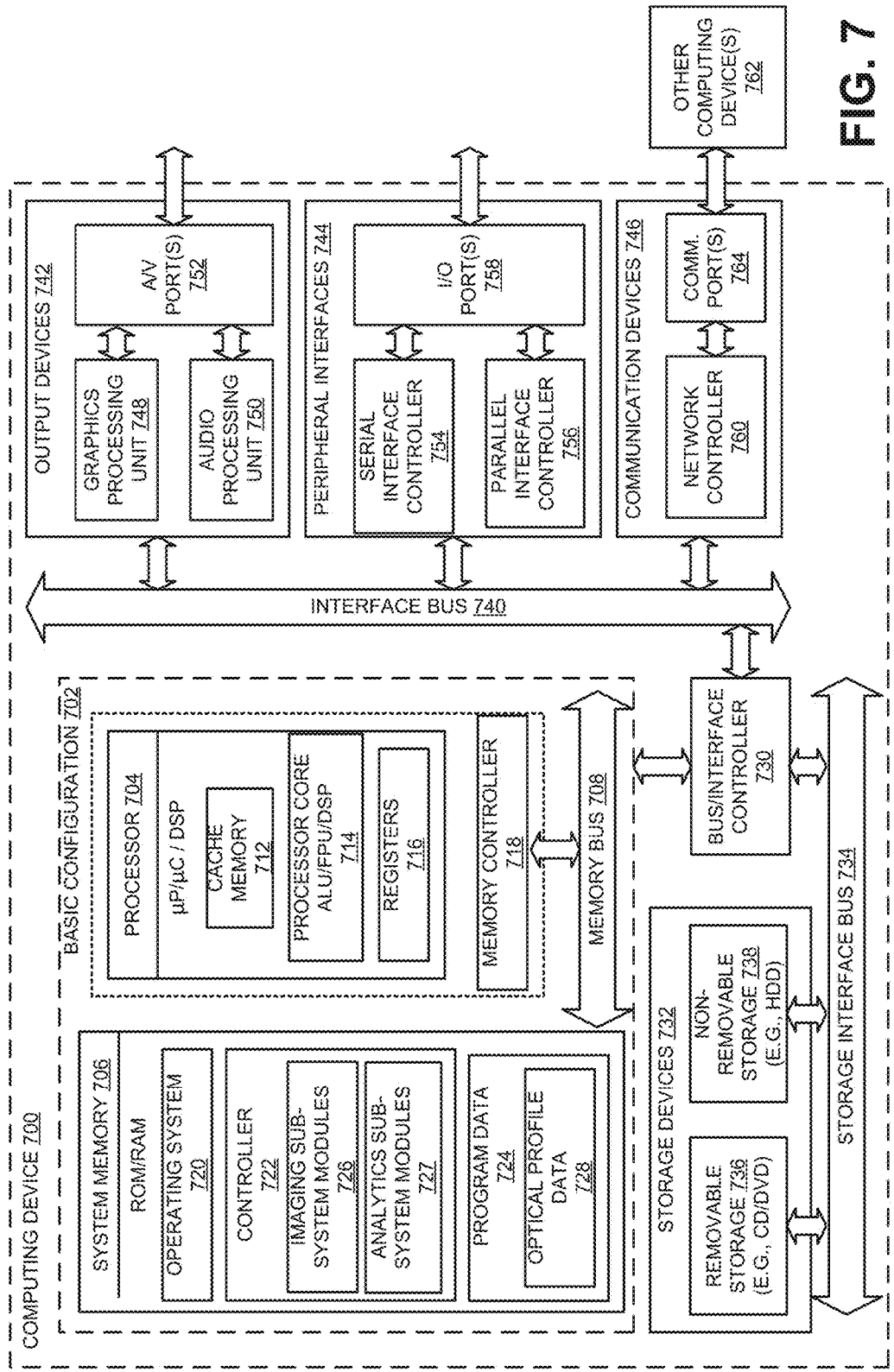
FIG. 7 illustrates a general purpose computing device, which may be used to implement real-time monitoring of material composition for quality control.

FIG. 7 illustrates a general purpose computing device, which may be used to implement real-time monitoring of material composition for quality control, arranged in accordance with at least some embodiments described herein.

For example, the computing device 700 may be used as a server, desktop computer, portable computer, smart phone, special purpose computer, or similar device such as a controller, a new component, a cluster of existing components in an operational system including a vehicle and a smart dwelling. In an example basic configuration 702, the computing device 700 may include one or more processors 704 and a system memory 706. A memory bus 708 may be used for communicating between the processor 704 and the system memory 706. The basic configuration 702 is illustrated in FIG. 7 by those components within the inner dashed line.

Depending on the desired configuration, the processor 704 may be of any type, including but not limited to a microprocessor (μP), a microcontroller (μC), a digital signal processor (DSP), or any combination thereof. The processor 704 may include one more levels of caching, such as a level cache memory 712, one or more processor cores 714, and registers 717. The example processor cores 714 may (each) include an arithmetic logic unit (ALU), a floating point unit (FPU), a digital signal processing core (DSP Core), or any combination thereof. An example memory controller 718 may also be used with the processor 704, or in some implementations the memory controller 718 may be an internal part of the processor 704.

Depending on the desired configuration, the system memory 706 may be of any type including but not limited to volatile memory (such as RAM), non-volatile memory (such as ROM, flash memory, etc.) or any combination thereof. The system memory 706 may include an operating system 720, a controller application 722, and program data 724. The controller application 722 may include one or more imaging sub-system modules 726 and analytics sub-system modules 727, which may be an integral part of the application or a separate application on its own. The imaging sub-system modules 726 may include an illumination module and a detection module. The illumination module may be configured to illuminate a liquid-based material with light from a plurality of illumination sources, where the illumination sources are activated by a controller according to a predefined sequence at different emission wavelengths. The detection module may be configured to detect light from the liquid-based material in response to the illumination at one or more detectors. The detected light may include light reflected from a first surface of the liquid-based material, light reflected from a second surface of the liquid-based material, and light transmitted through the first surface and the second surface of the liquid-based material. The analytics sub-system modules 727 may include a profiling module and a monitoring module. The profiling module may be configured to analyze the detected light to determine an optical profile of the liquid-based material. The monitoring module may be configured to monitor the determined optical profile in real-time to detect changes in the optical profile indicative of corresponding changes to a composition of the liquid-based material. The program data 724 may include, among other data, optical profile data 728 related to the detected light analysis used to determine the spectral profile, as described herein.

The computing device 700 may have additional features or functionality, and additional interfaces to facilitate communications between the basic configuration 702 and any desired devices and interfaces. For example, a bus/interface controller 730 may be used to facilitate communications between the basic configuration 702 and one or more data storage devices 732 via a storage interface bus 734. The data storage devices 732 may be one or more removable storage devices 736, one or more non-removable storage devices 738, or a combination thereof. Examples of the removable storage and the non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

The system memory 706, the removable storage devices 736 and the non-removable storage devices 738 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (for example, one or more output devices 742, one or more peripheral interfaces 744, and one or more communication devices 746) to the basic configuration 702 via the bus/interface controller 730. Some of the example output devices 742 include a graphics processing unit 748 and an audio processing unit 770, which may be configured to communicate to various external devices such as a display or speakers via one or more A/V ports 772. One or more example peripheral interfaces 744 may include a serial interface controller 774 or a parallel interface controller 776, which may be configured to communicate with external devices such as input devices (for example, keyboard, mouse, pen, voice input device, touch input device, etc.) or other peripheral devices (for example, printer, scanner, etc.) via one or more I/O ports 778. An example communication device 746 includes a network controller 760, which may be arranged to facilitate communications with one or more other computing devices 762 over a network communication link via one or more communication ports 764. The one or more other computing devices 762 may include servers, client devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 700 may be implemented as a part of a general purpose or specialized server, mainframe, or similar computer that includes any of the above functions. The computing device 700 may also be implemented as a personal computer including both laptop computer and non-laptop computer configurations.

Example embodiments may also include methods to implement real-time monitoring of material composition for quality control. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 8:
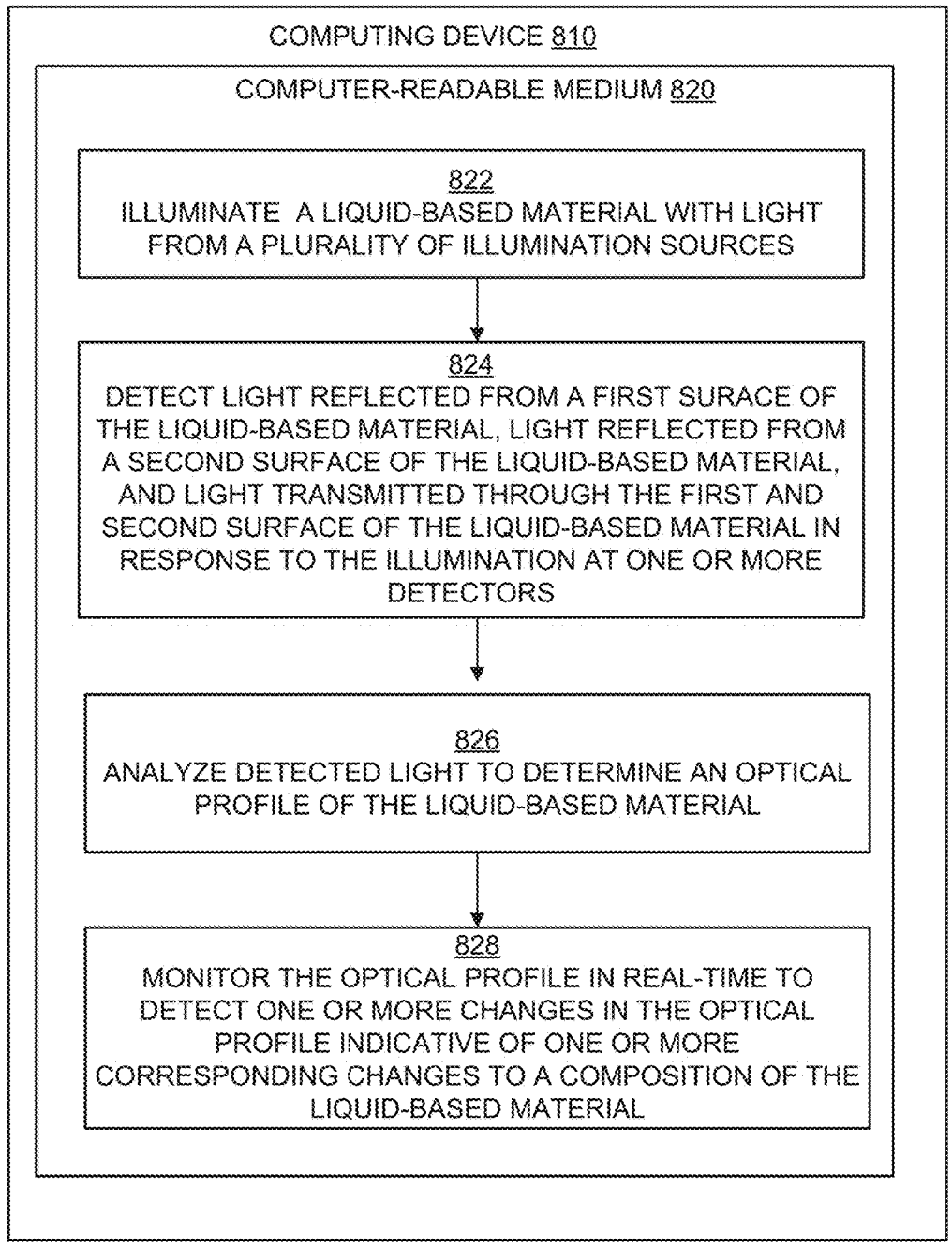
FIG. 8 is a flow diagram illustrating an example process to implement real-time monitoring of material composition for quality control that may be performed by a computing device such as the computing device in FIG. 7.

FIG. 8 is a flow diagram illustrating an example process to implement real-time monitoring of material composition for quality control that may be performed by a computing device such as the computing device in FIG. 7, arranged in accordance with at least some embodiments described herein.

Example methods may include one or more operations, functions or actions as illustrated by one or more of blocks 822, 824, 826, and/or 828. The operations described in the blocks 822 through 828 may also be stored as computer-executable instructions in a computer-readable medium such as a computer-readable medium 820 of a computing device 810.

An example process to implement real-time monitoring of material composition for quality control may begin with block 822, "ILLUMINATE A LIQUID-BASED MATERIAL WITH LIGHT FROM a PLURALITY OF ILLUMINATION SOURCES," where the illumination sources may be activated by a controller, each activated illumination source having a different emission wavelength. Upon sequential activation by the controller, the illumination sources may be configured to illuminate a liquid-based material with light, where the light may be incident on the liquid-based material through a first surface of the liquid based-material (or through a first portion of a container if the liquid-based material is contained). Light transmitted through the liquid based material may leave the liquid based material through the second surface of the liquid-based material (or through a second portion of the container if the liquid-based material is contained) after passing through the liquid-based material. The controller may be configured to select the illumination sources for activation based on a range of wavelengths transmitted by the liquid-based material. Furthermore, the controller may be configured to activate the one or more selected illumination sources according to a predefined sequence, where the sequence may be selected based on the range of wavelengths transmitted by the liquid-based material. In other embodiments, the controller may be configured to select the illumination sources for activation or the activation sequence based on a range of wavelengths reflected by the liquid-based material.

Block 822 may be followed by block 824, "DETECT LIGHT REFLECTED FROM A FIRST SURFACE OF THE LIQUID-BASED MATERIAL, LIGHT REFLECTED FROM A SECOND SURFACE OF THE LIQUID-BASED MATERIAL, AND LIGHT TRANSMITTED THROUGH THE FIRST SURFACE AND THE SECOND SURFACE OF THE LIQUID-BASED MATERIAL IN RESPONSE TO THE ILLUMINATION AT ONE OR MORE DETECTORS," where a first set of detectors are integrated with the illumination sources in an imaging device that is positioned proximal to the first surface of the liquid-based material (or the first portion of the container if the liquid-based material is contained). The first set of detectors may be configured to detect the light reflected from the first surface of the liquid-based material, and the light reflected from the second surface of the liquid-based material in response to the illumination. A second set of detectors may be positioned proximal to the second surface of the liquid-based material (or the second portion of the container if the liquid-based material is contained within a container). The second set of detectors may be configured to detect the light transmitted through the first surface and the second surface of the liquid-based material.

Block 824 may be followed by block 826, "ANALYZE DETECTED LIGHT TO DETERMINE AN OPTICAL PROFILE OF THE LIQUID-BASED MATERIAL," where the detected light may be analyzed to determine an optical profile of the liquid-based material based on an intensity of the reflection, transmission, and/or absorption of light at a respective wavelength at which the light was emitted from the illumination sources. The detected light may be analyzed by one or more processors of an analytics sub-system that is coupled to an imaging sub-system comprising the illumination sources, and the first and second set of detectors.

Block 826 may be followed by block 828, "MONITOR THE OPTICAL PROFILE IN REAL-TIME TO DETECT ONE OR MORE CHANGES IN THE OPTICAL PROFILE INDICATIVE OF CORRESPONDING CHANGES TO A COMPOSITION OF THE LIQUID-BASED MATERIAL," where the optical profile may be monitored in real-time to detect changes in the optical profile that may be indicative of corresponding changes to a composition of the liquid-based material. The optical profile may be monitored by the processors of the analytics sub-system, and in some examples, the optical profile may be displayed through a display device. One or more characteristics of the liquid-based material may also be evaluated by comparing the optical profile to an optical profile of a reference liquid-based material.

The blocks included in the above described process are for illustration purposes. Real-time monitoring of material composition for quality control may be implemented by similar processes with fewer or additional blocks. In some embodiments, the blocks may be performed in a different order. In some other embodiments, various blocks may be eliminated. In still other embodiments, various blocks may be divided into additional blocks, or combined together into fewer blocks.

FIG. 9 illustrates a block diagram of an example computer program product, arranged in accordance with at least some embodiments described herein.

In some embodiments, as shown in FIG. 9, the computer program product 900 may include a signal bearing medium 902 that may also include one or more machine readable instructions 904 that, when executed by, for example, a processor, may provide the functionality described herein. Thus, for example, referring to the processor 704 in FIG. 7, imaging sub-system modules 726 and analytics sub-system modules 727 executed on the processor 704 may undertake one or more of the tasks shown in FIG. 9 in response to the instructions 904 conveyed to the processor 704 by the medium 902 to perform actions associated with determination of a spectral profile of a sample as described herein. Some of those instructions may include, for example, one or more instructions to illuminate a liquid-based material with light from a plurality of illumination sources, detect light reflected from a first surface of the liquid-based material, light reflected from a second surface of the liquid-based material, and light transmitted through the first surface and the second surface of the liquid-based material in response to an illumination at one or more detectors, analyze detected light to determine an optical profile of the liquid-based material, and monitor the optical profile in real-time to detect one or more changes in the optical profile indicative of corresponding changes to a composition of the liquid-based material.

In some implementations, the signal bearing medium 902 depicted in FIG. 9 may encompass a computer-readable medium 906, such as, but not limited to, a hard disk drive, a solid state drive, a Compact Disc (CD), a Digital Versatile Disk (DVD), a digital tape, memory, etc. In some implementations, the signal bearing medium 902 may encompass a recordable medium 908, such as, but not limited to, memory, read/write (R/W) CDs, R/W DVDs, etc. In some implementations, the signal bearing medium 902 may encompass a communications medium 910, such as, but not limited to, a digital and/or an analog communication medium (for example, a fiber optic cable, a waveguide, a wired communications link, a wireless communication link, etc.). Thus, for example, the program product 900 may be conveyed to one or more modules of the processor 704 of FIG. 7 by an RF signal bearing medium, where the signal bearing medium 902 is conveyed by the wireless communications medium 910 (for example, a wireless communications medium conforming with the IEEE 802.11 standard).

In some examples, a liquid-based material may be comprise a liquid, and may further comprise one or more of dissolved chemical species, suspended particles, and the like. In some examples, a liquid-based material may comprise one or more liquid components. In some examples, a liquid-based material may comprise and one or more non-liquid components, such as suspended particles, colloidal particles, or other suspended components, and/or gas bubbles and the like. In some examples, an immiscible liquid component may be included in the form of an emulsion. In some examples, a liquid-based material may comprise one or more juices, such as one or more fruit juices, one or more vegetable juices, and the like. In some examples, a liquid-based material may comprise a liquid medium and an extract, for example a fruit or vegetable extract in an aqueous liquid medium. In some examples, a liquid medium may comprise fermentation products. In some examples, a liquid-based material may comprise a seasoning (such as salt), a flavoring, a sugar or other carbohydrate, a color, a preservative, and the like. Example liquid-based materials include fruit juice and/or a vegetable juice, either in raw (unprocessed) or in processed form. A liquid based material may be pre-processed, for example by sterilization, filtering, cooking, pasteurizing, and the like.

In some examples, a liquid-based material may be substantially non-scattering. In some examples, a liquid-based material may be cloudy, for example including appreciable solid components, such as fruit and/or vegetable solids. The transmission path length through the sample may be adjustable. In some examples, absorption at a plurality of wavelengths may be determined, and illumination wavelengths selected e.g. based on lower levels of absorption. In some examples, a carbonated liquid medium may be analyzed. In some examples, a larger collection area may be used to collect light, and the transmitted light may include scattered light having a scattering angle less than a predetermined threshold value.

In some examples, a liquid-based material may cause substantial attenuation (e.g. scattering and/or absorption) of light passing through the liquid-based material. However, radiometric data (such as ratios between transmitted amplitudes or intensities at different wavelengths) may be substantially unchanged by attenuation. In some examples, appropriate correction factors may be determined, e.g. in a calibration process, and used to correct for scattering or other optical effects. In some examples, a sub-set of a plurality of light sources may be selected based on the optical properties of the liquid-based medium, e.g. to reduce or substantially eliminate effects such as scattering, fluorescence, excessive absorption, and the like.

In some examples, a plurality of illumination sources may include light emitting diodes (LEDs), a multicolor LED, a laser, a light source filtered at one or more wavelengths, or other light source. In some examples, illumination sources may include one or more of white light sources, ultraviolet (UV) light sources, infrared light sources (such as near-IR light sources), red light sources, orange light sources, yellow light sources, green light sources, blue light sources, and violet light sources.

In some examples, a liquid-based material be a liquid, such as a mixture of two or more liquid components, or may consist essentially of a liquid, or may comprise a liquid. A liquid-based medium may flow, and in some examples may comprise one or more of a solution, a suspension, an emulsion, a colloidal dispersion, or other fluid material. In some examples, a liquid-based material may further comprise solid components (such as fruit or vegetable derived solids, such as pulp, insoluble materials, and the like). In some examples, a liquid-based material may further comprise gaseous components, such as carbonation.

In some examples, impurities (such as chemical impurities, or biological impurities such as bacteria) may be detected. In some examples, time-dependent processes may be monitored continuously or at intervals, for example fermentation, oxidation, mixing, chemical reactions, sterilization processes, bleaching, carbonation, filtering, centrifugation, and the like.

In some examples, a sample holder, such as a container, may be configured to hold a sample in a static state. In some examples, a container may be or include a conduit configured so that the sample flows through the container. In some examples, a sample holder may comprise a wall material that allows transmission of electromagnetic radiation at the illumination wavelengths. In some examples, a container may include one or more windows that allow electromagnetic radiation to enter or leave the sample. In some examples, an apparatus may be a hand-held device or other device with a portion configured to be dipped into a sample. In some examples, a sample may be probed with evanescent electromagnetic radiation using a prism or other optical element.

In some examples, spectroscopic information may be acquired from a fluid sample, such as a liquid-based sample, and used to analyze and/or evaluate the sample. Examples may include multiple light illumination sources configured to illuminate the sample with light, and one or more detectors configured to detect transmitted and/or reflected light from the sample in response to the illumination. For example, an example system may be configured to determine a spectral profile of any liquid, and in some examples the spectral profile may be monitored as a function of time. Example methods and apparatus may include quality control methods and apparatus, monitoring of a chemical reaction, compositional monitoring, and the like. Spectral profiles may be analyzed to identify one or more composition characteristics of a sample, for example a sample that may be derived from fruits and/or vegetables, for example for quality control purposes. In some examples, compositional monitoring may include determination of the concentration of one or more components in a sample, such as a liquid-based medium, for example a concentration of a fruit or other liquid concentrate, such as a syrup, in an aqueous medium.

In some examples, light transmitted through a sample may be detected, for example in addition to one or more of reflected light, fluorescent light, scattered light, or other optical signal from the sample. In some examples, an improved (e.g. more complete) optical profile of a sample may be determined, using one or more of reflected light, transmitted light, absorbed light, scattered light, fluorescent light, and the like, and in some examples in real time to enhance quality control.

In some examples, colorimetry may be used to monitor the appearance and quality of samples such as fruit or vegetable juice, for example in terms of visual appeal, ripeness, and/or nutrient content. In some examples, methods and apparatus may be used track physical and/or chemical changes of liquid-based materials such as fruit juice, fermentation products such as beer and wine, plant extracts, carbonated beverages, and the like. In some example, consistency in visual appearance may be improved by further processing the sample based on determined measurements. For example, a concentration of a component such as a fruit juice or a color may be adjusted to improve consistency, for example of a final retail product. In some examples, spoilage (such as oxidation or other degradation of one or more components) may be monitored, and in some examples a batch of a liquid-based material may be rejected based on measured spoilage being above a threshold. In some examples, concentration of a healthful component, such as an anti-oxidant, may be monitored and additional healthful component added to the liquid-based material based on concentration lower than a desired level.

A sample may be placed in, flow through, or otherwise be located with a container, such as a glass cuvette. In some examples, an apparatus be configured for the real time measurement of the amount of a constituent (such as a sugar, color or other additive, antioxidant, component correlated with fruit or vegetable ripeness, plant-derived color such as carotene, or other constituent) during formulation of a commercial liquid product such as a fruit juice, fermented liquid, carbonated beverage, and the like.

In some examples, an IR light source, such as a near-IR LED, and an associated IR-sensitive sensor may be used to detect sample constituents such as sugars in solution, or in some examples other organic components. In some examples, apparatus and methods allow improved monitoring of sugar content in sugar refineries, beverage plants, wineries, and the like. In some examples, an apparatus may be configured to provide a signal or display data correlated with a percentage Brix measurement.

In some examples, an apparatus may be calibrated using a reference liquid-based material of known composition. Calibration may be performed at intervals.

An example apparatus may include or be in communication with an electronic display on a vessel or barrel, a smart phone, or other display to report a current sample composition, provide alerts of process problems, and the like.

In some examples, an imaging sensor may be used to detect scattered light, and maybe used to collect more transmitted light than a single sensor element, and may be used to characterize scattering properties of a liquid-based sample.

In some examples, an apparatus may be constructed using a rugged exterior of metal, rubber and/or plastic to protect interior optical components. In some examples, an apparatus may comprise a body portion having illumination sources of different emission wavelengths and one or more sensors configured to detect light returned to the body portion when a sample is illuminated by the illumination sources, for example to determine reflected spectral data. In some examples, an apparatus may also comprise a second sensor portion that may be placed so as to detect light from the illumination sources after the light has been transmitted through a sample, for example to determined transmitted spectral data. Reflected and transmitted spectral data may be collected simultaneously or in an interleaved time-dependent manner. The second sensor portion may communicate wirelessly or through a cable with the body portion.

In some examples, an apparatus may be configured to communicate with a portable electronic device such as a smartphone, and a display of the smartphone used to display spectral data or other date determined from the collected sensor data.

According to some examples, an apparatus may be described. An example apparatus may include a plurality of illumination sources configured to illuminate a container with light, the container configured to contain a liquid-based material, and a controller configured to activate one or more of the illumination sources according to a predefined sequence, where each activated illumination source has a different emission wavelength. The example apparatus may also include one or more detectors configured to detect light transmitted through the liquid-based material in response to the illumination when the liquid-based material is contained in the container.

In some examples, the container may have a first portion through which the light is incident on the liquid-based material, where the illumination sources and the detectors are positioned proximal to the first portion of the container. The container may have a second portion through which transmitted light leaves the liquid based material after passing through the liquid based material, where the detectors may be positioned proximal to the second portion of the container such that the transmitted light is detected at the detectors. The illumination sources and the detectors may be aligned in a same horizontal plane and a same vertical plane, and a distance between the illumination sources and the detectors may be less than or equal to 1 centimeter. The detectors may be positioned adjacent to the illumination sources in a single imaging device.

In further examples, the example apparatus may include a reflective material configured to reflect light from each of the illumination sources back to at least one of the detectors. The controller may be configured to activate each of the illumination sources sequentially. The controller may be configured to select one or more of the illumination sources for activation based on a range of wavelengths transmitted by the liquid-based material. The controller may be further configured to select an activation sequence for the selected illumination sources based on a range of wavelengths transmitted by the liquid-based material. The illumination sources and the detectors may be integrated in an imaging sub-system.

In yet further examples, the apparatus may be communicatively coupled to an analytics sub-system through wired or wireless communication media, the analytics sub-system configured to analyze detected light to determine a optical profile of the liquid-based material, where the analytics sub-system may be further configured to monitor the optical profile of the liquid-based material in real-time to detect a change in the optical profile. The analytics sub-system may be integrated with the illumination sources and the detectors, and the apparatus may further include a display device configured to display the monitored optical profile. The illumination sources may be light emitting diodes (LEDs), where the LEDs have different emission wavelengths. The detectors may be photodiodes, photomultiplier tubes, complementary metal oxide semiconductor (CMOS) image sensors, charged coupled devices (CCDs), and/or microchannel plates. The liquid-based material may include a fruit juice and a vegetable juice.

According to other embodiments, systems configured to monitor composition of a liquid-based material may be described. An example system may include an imaging sub-system and an analytics sub-system coupled to the imaging sub-system. The imaging sub-system may include a plurality of illumination sources configured to illuminate the liquid-based material with light, a controller configured to activate one or more of the illumination sources according to a predefined sequence, where each activated illumination source has a different emission wavelength, and one or more detectors configured to detect one or more of light reflected from a first surface of the liquid-based material, light reflected from a second surface of the liquid-based material, and light transmitted through the first surface and the second surface of the liquid-based material in response to the illumination. The analytics sub-system may include one or more processors configured to analyze detected light to determine an optical profile of the liquid-based material, and monitor the optical profile of the liquid-based material in real-time to detect one or more changes in the optical profile indicative of one or more corresponding changes to a composition of the liquid-based material.

In other embodiments, at least one of the detectors may be an image sensor configured to capture an image of the light transmitted through the first surface and the second surface of the liquid-based material in response to the illumination. The liquid-based material may be contained within a container composed of crystal, silicon-based material, or plastic. The container may be an extension of a vessel containing the liquid-based material. The illumination sources and the detectors may be joined through a connector configured to enable the imaging sub-system to attach onto the container.

In further embodiments, the liquid-based material may be contained within a vessel, and the imaging sub-system is immersed in the liquid-based material within the vessel. A display device may be integrated with an external surface of the vessel. The controller may be configured to select the one or more of the illumination sources for activation based on a range of wavelengths reflected by the liquid-based material. The controller may be further configured to select an activation sequence for the selected illumination sources based on the range of wavelengths reflected by the liquid-based material.

According to some examples, methods to monitor composition of a liquid-based material are provided. An example method may include illuminating the liquid-based material with light from a plurality of illumination sources, detecting one or more of light reflected from a first surface of the liquid-based material, light reflected from a second surface of the liquid-based material, and light transmitted through the first surface and the second surface of the liquid-based material in response to the illumination at one or more detectors, analyzing detected light to determine an optical profile of the liquid-based material, and monitoring the optical profile of the liquid-based material in real-time to detect one or more changes in the optical profile indicative of one or more corresponding changes to a composition of the liquid-based material.

In other examples, an intensity of the light reflected from the first surface of the liquid-based material and the light reflected from the second surface of the liquid-based material in response to the illumination may be determined, and may be determined the optical profile based on a comparison of the intensity of the light reflected from the first surface of the liquid-based material and the light reflected from the second surface of the liquid-based material to an intensity of light transmitted from the illumination sources. An intensity of the light transmitted through the first surface and the second surface of the liquid-based material in response to the illumination may be determined, a transmittance may be determined based on the intensity of the light transmitted through the first surface and the second surface of the liquid-based material and an intensity of the light emitted from the illumination sources, and an absorbance may be determined based on the transmittance.

In further examples, one or more characteristics of the liquid-based material may be evaluated based on the optical profile. The optical profile of the liquid-based material and an optical profile of a reference liquid-based material may be compared to evaluate the characteristics of the liquid-based material. While various compositions, methods, systems, and devices are described in terms of "comprising" various components or steps (interpreted as meaning "including, but not limited to"), the compositions, methods, systems, and devices can also "consist essentially of" or "consist of" the various components and steps, and such terminology should be interpreted as defining essentially closed-member groups."

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, may be equivalently implemented in integrated circuits, as one or more computer programs running on one or more computers (for example, as one or more programs running on one or more computer systems), as one or more programs running on one or more processors (for example as one or more programs running on one or more microprocessors), as firmware, or as virtually any combination thereof, and that designing the circuitry and/or writing the code for the software and or firmware would be possible in light of this disclosure.

The present disclosure is not to be limited in terms of the particular embodiments described in this application, which are intended as illustrations of various aspects. Many modifications and variations can be made without departing from its spirit and scope Functionally equivalent methods and apparatuses within the scope of the disclosure, in addition to those enumerated herein, will be possible from the foregoing descriptions. Such modifications and variations are intended to fall within the scope of the appended claims. The present disclosure includes the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular embodiments only, and is not intended to be limiting.

In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (for example, a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that particular functionality is achieved. Hence, any two components herein combined to achieve a particular functionality may be seen as "associated with" each other such that the particular functionality is achieved, irrespective of architectures or intermediate components. Likewise, any two components so associated may also be viewed as being "operably connected", or "operably coupled", to each other to achieve the particular functionality, and any two components capable of being so associated may also be viewed as being "operably couplable", to each other to achieve the particular functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A system configured to monitor composition of a liquid-based material, the system comprising:
    an imaging sub-system comprising:
        a plurality of illumination sources configured to illuminate the liquid-based material with light, wherein the liquid-based material includes a first surface and a second surface, and wherein the second surface is opposite to the first surface;
        a controller configured to activate one or more of the plurality of illumination sources according to a particular sequence, wherein each activated illumination source includes a different emission wavelength;
        a first set of detectors positioned adjacent to the plurality of illumination sources and proximal to the first surface of the liquid-based material, wherein the first set of detectors is configured to detect light reflected from the first surface of the liquid-based material and detect light reflected from the second surface of the liquid-based material and wherein the first set of detectors includes a first image sensor that is configured to capture a first image of the light reflected from the first surface and the second surface of the liquid-based material in response to illumination;
        a second set of detectors positioned proximal to the second surface of the liquid-based material, wherein the second set of detectors is configured to detect light transmitted through the liquid-based material; and
    an analytics sub-system coupled to the imaging sub-system, wherein the analytics sub-system comprises one or more processors, wherein the one or more processors are configured to:
        analyze the first image and the detected light to determine an optical profile of the liquid-based material, wherein the analysis of the detected light comprises determination of an intensity of reflection, transmittance, and absorbance of the detected light by the first set of detectors and the second set of detectors; and
        monitor the optical profile of the liquid-based material in real-time to detect one or more changes, in the optical profile, indicative of one or more corresponding changes to a composition of the liquid-based material.

2. The system of claim 1, wherein at least one of the second set of detectors is a second image sensor, and wherein the second image sensor is configured to capture a second image of the light transmitted through the first surface and the second surface of the liquid-based material in response to the illumination.

3. The system of claim 1, wherein the liquid-based material is contained within a container that comprises at least one wall transparent to the light from the plurality of illumination sources.

4. The system of claim 3, wherein the container is an extension of a vessel that contains the liquid-based material.

5. The system of claim 4, wherein the plurality of illumination sources and the first set of detectors are joined through a connector, and wherein the connector is configured to enable the imaging sub-system to attach onto the container.

6. The system of claim 1, wherein the liquid-based material is contained within a vessel, and wherein the imaging sub-system is immersed in the liquid-based material within the vessel.

7. The system of claim 6, further comprising a display device integrated with an external surface of the vessel.

8. The system of claim 1, wherein the controller is configured to select the one or more of the plurality of illumination sources for activation based on a range of wavelengths reflected by the liquid-based material.

9. The system of claim 8, wherein the controller is further configured to select an activation sequence for the selected one or more of the plurality of illumination sources based on the range of wavelengths reflected by the liquid-based material.

10. The system of claim 1, wherein the first set of detectors are located opposite from the second set of detectors.

11. The system of claim 1, wherein the imaging sub-system further includes a conduit that circulates the liquid-based material, the conduit includes a first window through which the first set of detectors detect the light reflected from the first surface, and the conduit includes a second window through which the second set of detectors detect the light transmitted through the liquid-based material.

12. The system of claim 11, wherein the conduit is a tube or a pipe.

13. The system of claim 11, wherein the conduit is composed of at least one of crystal, a silicon-based material, or plastic.

14. The system of claim 1, wherein the imaging sub-system is a closed system that does not break an airlock in order to monitor the composition of the liquid-based material.

* * * * *